US 11,760,768 B2

(12) United States Patent
Barik et al.

(10) Patent No.: US 11,760,768 B2
(45) Date of Patent: Sep. 19, 2023

(54) MOLYBDENUM(0) PRECURSORS FOR DEPOSITION OF MOLYBDENUM FILMS

(71) Applicant: Applied Materials, Inc., Santa Clara, CA (US)

(72) Inventors: Chandan Kr Barik, Singapore (SG); John Sudijono, Singapore (SG); Chandan Das, Singapore (SG); Doreen Wei Ying Yong, Singapore (SG); Mark Saly, Santa Clara, CA (US); Bhaskar Jyoti Bhuyan, San Jose, CA (US); Feng Q. Liu, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 17/236,020

(22) Filed: Apr. 21, 2021

(65) Prior Publication Data
US 2022/0356197 A1   Nov. 10, 2022

(51) Int. Cl.
*C07F 11/00* (2006.01)
*C23C 16/455* (2006.01)
*C23C 16/44* (2006.01)
*C23C 16/02* (2006.01)
*C23C 16/18* (2006.01)
*C23C 16/56* (2006.01)

(52) U.S. Cl.
CPC ........ *C07F 11/005* (2013.01); *C23C 16/0272* (2013.01); *C23C 16/18* (2013.01); *C23C 16/4408* (2013.01); *C23C 16/45527* (2013.01); *C23C 16/45553* (2013.01); *C23C 16/56* (2013.01); *C23C 16/0209* (2013.01); *C23C 16/0227* (2013.01)

(58) Field of Classification Search
CPC .............................. C07F 11/005; C23C 16/18
See application file for complete search history.

(56) References Cited

U.S. PATENT DOCUMENTS

| 3,103,527 A | 9/1963 | Panson et al. |
| 4,992,305 A | 2/1991 | Erbil |

(Continued)

FOREIGN PATENT DOCUMENTS

| CN | 111747994 A | 10/2020 |
| CN | 111777649 A | 10/2020 |

(Continued)

OTHER PUBLICATIONS

Zhu et al; Oxidative addition of dihydrogen to (n6-arene) Mo(PMe3)3 complexes: origin of the naphthalene and anthracene effects; J. Am. Chem. Soc.; 2006; 128; pp. 5452-5461. (Year: 2006).*

(Continued)

*Primary Examiner* — Elizabeth A Burkhart
(74) *Attorney, Agent, or Firm* — Servilla Whitney LLC

(57) ABSTRACT

Molybdenum(0) and coordination complexes are described. Methods for depositing molybdenum-containing films on a substrate are described. The substrate is exposed to a molybdenum precursor and a reactant to form the molybdenum-containing film (e.g., elemental molybdenum, molybdenum oxide, molybdenum carbide, molybdenum silicide, molybdenum disulfide, molybdenum nitride). The exposures can be sequential or simultaneous.

1 Claim, 1 Drawing Sheet

(56) References Cited

U.S. PATENT DOCUMENTS

| | | | |
|---|---|---|---|
| 5,130,172 | A | 7/1992 | Hicks et al. |
| 7,390,360 | B2 | 7/2008 | Shenai-Khatkhate et al. |
| 8,148,564 | B2 | 4/2012 | Winter et al. |
| 9,109,281 | B2 * | 8/2015 | Gatineau ............... C01G 25/02 |
| 9,175,023 | B2 | 11/2015 | Odedra et al. |
| 9,255,327 | B2 | 2/2016 | Winter et al. |
| 9,540,730 | B2 | 1/2017 | Winter |
| 9,587,117 | B2 | 3/2017 | Yerushalmi et al. |
| 9,695,207 | B2 | 7/2017 | Sato et al. |
| 9,802,220 | B2 | 10/2017 | Heys et al. |
| 9,881,796 | B2 | 1/2018 | Sato et al. |
| 9,932,671 | B2 | 4/2018 | Blackwell et al. |
| 10,079,144 | B2 | 9/2018 | Kim et al. |
| 10,745,430 | B2 | 8/2020 | Garratt et al. |
| 2005/0215805 | A1 | 9/2005 | Meiere |
| 2006/0068100 | A1 | 3/2006 | Machida et al. |
| 2007/0154637 | A1 | 7/2007 | Vinayak et al. |
| 2013/0202794 | A1 | 8/2013 | Dussarrat et al. |
| 2016/0002786 | A1 | 1/2016 | Gatineau et al. |
| 2016/0133837 | A1 | 5/2016 | Hsueh et al. |
| 2017/0058401 | A1 * | 3/2017 | Blackwell ......... H01L 21/28556 |
| 2017/0330748 | A1 | 11/2017 | Pickett et al. |
| 2018/0265975 | A1 | 9/2018 | Winter et al. |
| 2018/0294187 | A1 | 10/2018 | Thombare et al. |
| 2019/0003050 | A1 | 1/2019 | Dezelah et al. |
| 2019/0067003 | A1 | 2/2019 | Zope et al. |
| 2019/0067094 | A1 | 2/2019 | Zope et al. |
| 2019/0088555 | A1 | 3/2019 | Xie et al. |
| 2019/0226086 | A1 | 7/2019 | Wright et al. |
| 2019/0301010 | A1 | 10/2019 | Winter et al. |
| 2020/0283898 | A1 | 9/2020 | Choi et al. |
| 2020/0343358 | A1 | 10/2020 | Zhu et al. |
| 2022/0220607 | A1 * | 7/2022 | Leoncini ................ C07F 17/00 |

FOREIGN PATENT DOCUMENTS

| | | |
|---|---|---|
| FR | 2314263 A1 | 1/1977 |
| GB | 832142 | 4/1960 |
| WO | 2008039960 A1 | 4/2008 |
| WO | 2020076502 A1 | 4/2020 |
| WO | 202010336 A1 | 5/2020 |
| WO | 2020185618 A1 | 9/2020 |

OTHER PUBLICATIONS

Ashworth, Edward F., et al., "Some Studies of q-Cycloheptatrienylmolybdenum Compounds", Common Metals, 1974, 36, 213; J.C.S. Chem. Comm., 1974, 5.

Bertuch, Adam, et al., "Atomic layer deposition of molybdenum oxide using bis(tertbutylimido) bis(dimethylamido) molybdenum", J. Vac. Sci. Technol. A 32, 01A119 (2014); https://doi.org/10.1116/1.4843595.

Bertuch, Adam, et al., "Plasma enhanced atomic layer deposition of molybdenum carbide and nitride with bis(tert-butylimido)bis(dimethylamido) molybdenum", Journal of Vacuum Science & Technology A 35, 01B141 (2017); doi: 10.1116/1.4972776.

Breeze, Roy, et al., "The chemistry of cycloheptatrienyl complexes of molybdenum and tungsten: synthesis and substitution chemistry of some new carbonylacetonitrile derivatives", Journal of Organometallic Chemistry, 356 (1988) 343-353.

Drake, Tasha L., et al., "Vapor deposition of molybdenum oxide using bis(ethylbenzene) molybdenum and water", Journal of Vacuum Science & Technology A 34, 051403 (2016); doi: 10.1116/1.4959532.

El-Kadri, Oussama M., et al., "Film growth precursor development for metal nitrides. Synthesis, structure, and volatility of molybdenum(VI) and tungsten(VI) complexes containing bis(imido)metal fragments and various nitrogen donor ligands", Dalton Trans., 2006, 1943-1953.

El-Kadri, Oussama M., et al., "Synthesis and characterization of two dioxidomolybdenum(VI) complexes bearing amidinato and pyrazolato ligands and their use in thin film growth and oxygen atom transfer reactions", Polyhedron 147 (2018) 36-41.

Green, Malcolm L.H., et al., "A Comparison of the Rates of Intramolecular Hydrogen Migration in the Molecules [Mo(q-C,H,),]"+ to give [Mo(q-C,H,)(q-C,H,)]"+, n=0 or 1 : Crystal Structures of [Mo(q-C,H,),], [Mo(q-C,H,)(q-C,H,)], and [Mo(q-C,H,),] [BF,] *", J. Chem. Soc. Dalton Trans. 1989, 331-343.

Green, Jennifer C., et al., "Molybdenum-95 and Carbon-13 Nuclear Magnetic Shielding and Bonding Relationships in Sandwich Complexes", J. Chem. Soc. Dalton Trans. 1986, 1313-1316.

Green, Malcolm L.H., et al., "n-Cycloheptatrienyl-Molybdenumenum Chemistry: Tertiary Phosphine, Alkyl, Hydrido, Halogeno and Related Derivatives", Polyhedron vol. 4, No. 6, pp. 1035-1041, 1985.

Green, Malcolm L.H., et al., "New Synthetic Pathways in q-Cycloheptatrienyl Molybdenum Chemistry", J. Chem. Soc., Chem. Commuy., 1992, 918-919.

Green, Malcom L.H., et al., "Synthesis and Reactions of q-Cycloheptatrienyl Derivatives of Molybdenum", J. Chem. Soc. Dalton Trans. 1993, 3203-3212.

Jurca, T., et al., "Second-generation hexavalent molybdenum oxoamidinate precursors for atomic layer deposition†", Dalton Trans., 2017, 46, 1172.

Land, Michael A., et al., "Ligand-Assisted Volatilization and Thermal Stability of Bis(imido)dichloromolybdenum(VI) ([(t-BuN✪)2MoCl2]2) and Its Adducts", Organometallics XXXX, XXX, XXX-XXX.

Miikkulainen, Ville, et al., "Bis(tert-butylimido)-bis(dialkylamido) Complexes of Molybdenum as Atomic Layer Deposition (ALD) Precursors for Molybdenum Nitride: the Effect of the Alkyl Group***", Chem. Vap. Deposition 2008, 14, 71-77.

Mouat, Aidan R., et al., "Volatile Hexavalent Oxo-amidinate Complexes: Molybdenum and Tungsten Precursors for Atomic Layer Deposition", Chem. Mater. 2016, 28, 1907-1919.

Vos, Martijn F.J., et al., "Atomic layer deposition of molybdenum oxide from (NtBu)2(NMe2)2Mo and O2 plasma", J. Vac. Sci. Technol. A 34, 01A103 (2016); https://doi.org/10.1116/1.4930161.

PCT International Search Report and Written Opinion in PCT/US2022/025459 dated Aug. 12, 2022, 12 pages.

Bezdek, M. J., et al., "Coordination-induced weakening of ammonia, water, and hydrazine X-H bonds in a molybdenum complex", Science, 2016, vol. 354, No. 6313, pp. 730-733.

Brookhart, M., et al., "Hexakis(trimethyl phosphine) molybdenum chemistry: dinitrogen, ethylene, butadiene, η-cyclopentadienyl, and related derivatives", Journal of the chemical society, dalton transactions, 1985, No. 3, pp. 423-433.

Sattler, A., "Chemistry of highly reactive group 5 and 6 transition metal compounds: modeling aspects of the industrial hydrotreating process and synthesis of the first transition metal complexes that feature a [CCC] X3-donor pincer ligand", in partial fulfillment of the requirements for the degree of doctor of philosophy in the graduate school of arts and sciences, Columbia university, 2012, pp. 1-452.

Wang, Y., et al., "Interaction of molybdenum hexacarbonyl with metallic aluminum at high temperatures: carbide and alloy formation", Journal of molecular catalysis A: Chemical, 2005, vol. 236, pp. 18-31.

* cited by examiner

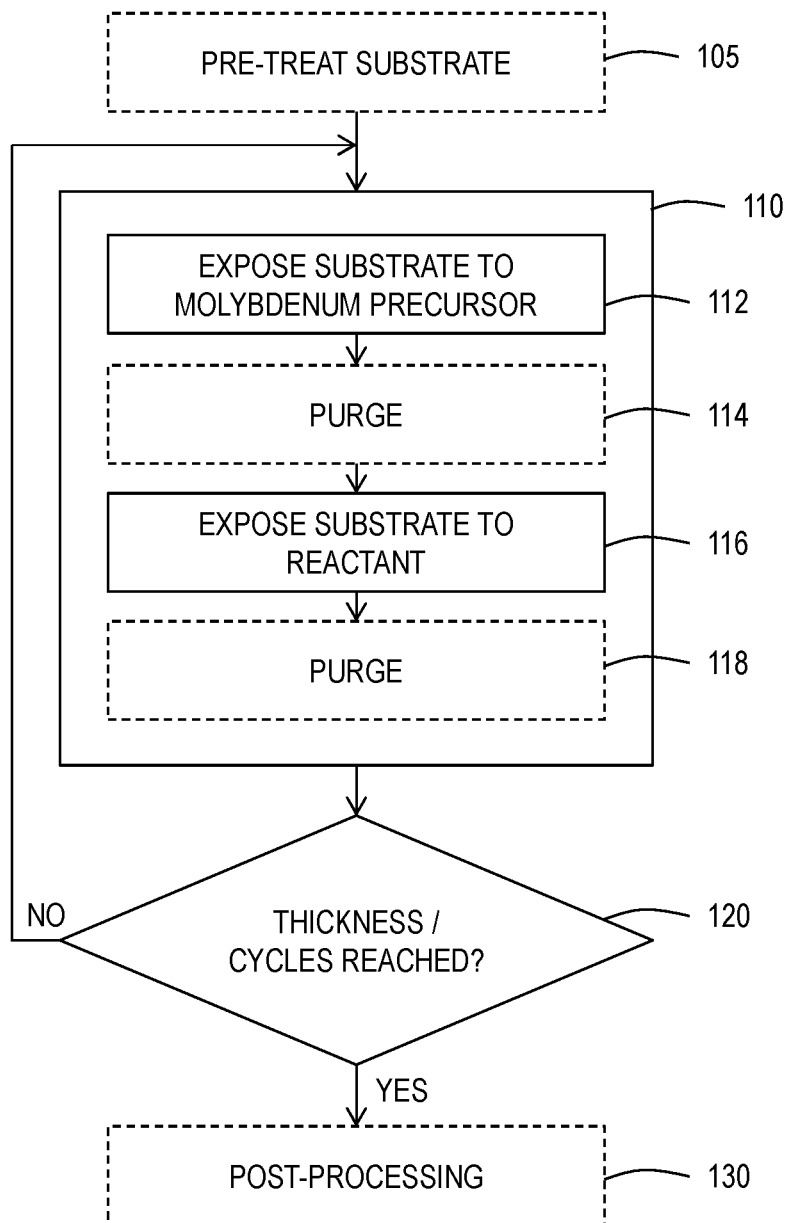

MOLYBDENUM(0) PRECURSORS FOR DEPOSITION OF MOLYBDENUM FILMS

TECHNICAL FIELD

Embodiments of the disclosure relate to molybdenum precursors and methods for depositing molybdenum-containing films. More particularly, embodiments of the disclosure are directed to molybdenum(0) complexes containing 2n-electron donor neutral mono-, bi-, and tri-dentate ligands and methods of use thereof.

BACKGROUND

The semiconductor processing industry continues to strive for larger production yields while increasing the uniformity of layers deposited on substrates having larger surface areas. These same factors in combination with new materials also provide higher integration of circuits per unit area of the substrate. As circuit integration increases, the need for greater uniformity and process control regarding layer thickness rises. As a result, various technologies have been developed to deposit layers on substrates in a cost-effective manner, while maintaining control over the characteristics of the layer.

Chemical vapor deposition (CVD) is one of the most common deposition processes employed for depositing layers on a substrate. CVD is a flux-dependent deposition technique that requires precise control of the substrate temperature and the precursors introduced into the processing chamber in order to produce a desired layer of uniform thickness. These requirements become more critical as substrate size increases, creating a need for more complexity in chamber design and gas flow technique to maintain adequate uniformity.

A variant of CVD that demonstrates excellent step coverage is cyclical deposition or atomic layer deposition (ALD). Cyclical deposition is based upon atomic layer epitaxy (ALE) and employs chemisorption techniques to deliver precursor molecules on a substrate surface in sequential cycles. The cycle exposes the substrate surface to a first precursor, a purge gas, a second precursor and the purge gas. The first and second precursors react to form a product compound as a film on the substrate surface. The cycle is repeated to form the layer to a desired thickness.

The advancing complexity of advanced microelectronic devices is placing stringent demands on currently used deposition techniques. Unfortunately, there is a limited number of viable chemical precursors available that have the requisite properties of robust thermal stability, high reactivity, and vapor pressure suitable for film growth to occur. In addition, precursors that often meet these requirements still suffer from poor long-term stability and lead to thin films that contain elevated concentrations of contaminants such as oxygen, nitrogen, and/or halides that are often deleterious to the target film application.

Molybdenum and molybdenum-based films have attractive material and conductive properties. These films have been proposed and tested for applications from front end to back end parts of semiconductor and microelectronic devices. Processing a molybdenum precursor often involves use of halogen and carbonyl-based substituents. These ligands provide sufficient stability at the expense of reduced reactivity, increasing process temperature. There is, therefore, a need in the art for molybdenum precursors that are free of halogen groups that react to form molybdenum metal and molybdenum-based films.

SUMMARY

One or more embodiments of the disclosure are directed to metal coordination complexes. In one or more embodiments, a metal coordination complex comprises molybdenum(0) and having a structure of Formula (I), Formula (II), or Formula (III):

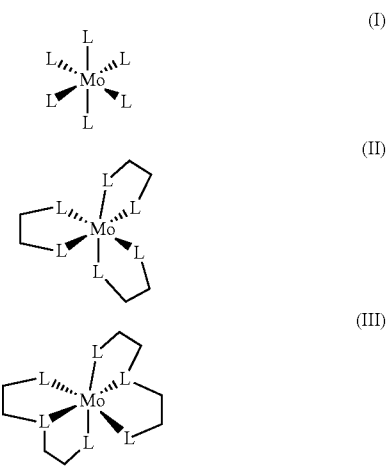

wherein L is one or more of a 2n-electron donor neutral monodentate ligand, 2n-electron donor neutral bidentate ligand, and a 2n-electron donor neutral tridentate ligand, the metal coordination complex substantially free of halogen and substantially free of a Mo—O bond.

One or more embodiments of the disclosure are directed to a method of depositing a film. In one or more embodiments, a method of depositing a film comprises: exposing a substrate to a molybdenum(0) precursor; and exposing the substrate to a reactant to form a molybdenum-containing film on a substrate surface, the molybdenum-containing film substantially free of halogen.

Further embodiments of the disclosure are directed to methods of depositing a film. In one or more embodiments, a method of depositing a film comprises: forming a molybdenum-containing film in a process cycle comprising sequential exposure of a substrate to a molybdenum(0) precursor, purge gas, reactant, and purge gas.

BRIEF DESCRIPTION OF THE DRAWINGS

So that the manner in which the above recited features of the disclosure can be understood in detail, a more particular description of the disclosure, briefly summarized above, may be had by reference to embodiments, some of which are illustrated in the appended drawings. It is to be noted, however, that the appended drawings illustrate only typical embodiments of the disclosure and are therefore not to be considered limiting of its scope, for the disclosure may admit to other equally effective embodiments.

FIG. 1 illustrates a process flow diagram of a method in accordance with one or more embodiments of the disclosure.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Embodiments of the disclosure provide precursors and processes for depositing molybdenum-containing films. These metal coordination complexes of one or more embodiments are substantially free of halogens and molybdenum oxygen bonds. The ligand may be 2n-electron donor neutral mono-, bi-, and tri-dentate ligands. The bonding between the ligands provides additional stability under ALD and CVD conditions. The process of various embodiments uses vapor deposition techniques, such as an atomic layer deposition (ALD) or chemical vapor deposition (CVD) to provide molybdenum films. The molybdenum precursors of one or more embodiments are volatile and thermally stable, and, thus, suitable for vapor deposition.

In one or more embodiments, the molybdenum precursor is free of halogen. In other embodiments, the molybdenum precursor is free of molybdenum oxygen (Mo—O) bonds. In one or more embodiments, the molybdenum precursor if free of halogen and is free of molybdenum oxygen (Mo—O) bonds.

As used herein, the term "substantially free" means that there is less than less than about 5%, including less than about 4%, less than about 3%, less than about 2%, less than about 1%, and less than about 0.5% of halogen, on an atomic basis, in the molybdenum-containing film. In some embodiments, the molybdenum-containing film is substantially free of molybdenum oxygen (Mo—O) bonds, and there is less than about 10%, less than about 9%, less than about 8%, less than about 7%, less than about 6%, less than about 5%, including less than about 4%, less than about 3%, less than about 2%, less than about 1%, and less than about 0.5% of molybdenum oxygen bonds, on an atomic basis, in the molybdenum-containing film.

A "substrate" as used herein, refers to any substrate or material surface formed on a substrate upon which film processing is performed during a fabrication process. For example, a substrate surface on which processing can be performed include materials such as silicon, silicon oxide, strained silicon, silicon on insulator (SOI), carbon doped silicon oxides, amorphous silicon, doped silicon, germanium, gallium arsenide, glass, sapphire, and any other materials such as metals, metal oxides, metal nitrides, metal alloys, and other conductive materials, depending on the application. Substrates include, without limitation, semiconductor wafers. Substrates may be exposed to a pretreatment process to polish, etch, reduce, oxidize, hydroxylate, anneal and/or bake the substrate surface. In addition to film processing directly on the surface of the substrate itself, in the present invention, any of the film processing steps disclosed may also be performed on an underlayer formed on the substrate as disclosed in more detail below, and the term "substrate surface" is intended to include such underlayer as the context indicates. Thus, for example, where a film/layer or partial film/layer has been deposited onto a substrate surface, the exposed surface of the newly deposited film/layer becomes the substrate surface.

According to one or more embodiments, the method uses an atomic layer deposition (ALD) process. In such embodiments, the substrate surface is exposed to the precursors (or reactive gases) sequentially or substantially sequentially. As used herein throughout the specification, "substantially sequentially" means that a majority of the duration of a precursor exposure does not overlap with the exposure to a co-reagent, although there may be some overlap.

As used in this specification and the appended claims, the terms "precursor", "reactant", "reactive gas" and the like are used interchangeably to refer to any gaseous species that can react with the substrate surface.

"Atomic layer deposition" or "cyclical deposition" as used herein refers to the sequential exposure of two or more reactive compounds to deposit a layer of material on a substrate surface. As used in this specification and the appended claims, the terms "reactive compound", "reactive gas", "reactive species", "precursor", "process gas" and the like are used interchangeably to mean a substance with a species capable of reacting with the substrate surface or material on the substrate surface in a surface reaction (e.g., chemisorption, oxidation, reduction). The substrate, or portion of the substrate is exposed sequentially to the two or more reactive compounds which are introduced into a reaction zone of a processing chamber. In a time-domain ALD process, exposure to each reactive compound is separated by a time delay to allow each compound to adhere and/or react on the substrate surface. In a spatial ALD process, different portions of the substrate surface, or material on the substrate surface, are exposed simultaneously to the two or more reactive compounds so that any given point on the substrate is substantially not exposed to more than one reactive compound simultaneously. As used in this specification and the appended claims, the term "substantially" used in this respect means, as will be understood by those skilled in the art, that there is the possibility that a small portion of the substrate may be exposed to multiple reactive gases simultaneously due to diffusion, and that the simultaneous exposure is unintended.

In one aspect of a time-domain ALD process, a first reactive gas (i.e., a first precursor or compound A) is pulsed into the reaction zone followed by a first time delay. Next, a second precursor or compound B is pulsed into the reaction zone followed by a second delay. During each time delay a purge gas, such as argon, is introduced into the processing chamber to purge the reaction zone or otherwise remove any residual reactive compound or by-products from the reaction zone. Alternatively, the purge gas may flow continuously throughout the deposition process so that only the purge gas flows during the time delay between pulses of reactive compounds. The reactive compounds are alternatively pulsed until a desired film or film thickness is formed on the substrate surface. In either scenario, the ALD process of pulsing compound A, purge gas, compound B and purge gas is a cycle. A cycle can start with either compound A or compound B and continue the respective order of the cycle until achieving a film with the desired thickness. In some embodiments, there may be two reactants, A and B, that are alternatingly pulsed and purged. In other embodiments, there may be three or more reactants, A, B, and C, that are alternatingly pulsed and purged.

In an aspect of a spatial ALD process, a first reactive gas and second reactive gas (e.g., hydrogen radicals) are delivered simultaneously to the reaction zone but are separated by an inert gas curtain and/or a vacuum curtain. The substrate is moved relative to the gas delivery apparatus so that any given point on the substrate is exposed to the first reactive gas and the second reactive gas.

Without intending to be bound by theory, it is thought that the presence of halogens in the structure of molybdenum (Mo) precursors can pose challenges, as halogen contamination may affect device performance and hence require additional removal procedures.

Molybdenum (Mo) can be grown by atomic layer deposition or chemical vapor deposition for many applications.

One or more embodiments of the disclosure advantageously provide processes for atomic layer deposition or chemical vapor deposition to form molybdenum-containing films. As used in this specification and the appended claims, the term "molybdenum-containing film" refers to a film that comprises molybdenum atoms and has greater than or equal to about 1 atomic % molybdenum, greater than or equal to about 2 atomic % molybdenum, greater than or equal to about 3 atomic % molybdenum, greater than or equal to about 4 atomic % molybdenum, greater than or equal to about 5 atomic % molybdenum, greater than or equal to about 10 atomic % molybdenum, greater than or equal to about 15 atomic % molybdenum, greater than or equal to about 20 atomic % molybdenum, greater than or equal to about 25 atomic % molybdenum, greater than or equal to about 30 atomic % molybdenum, greater than or equal to about 35 atomic % molybdenum, greater than or equal to about 40 atomic % molybdenum, greater than or equal to about 45 atomic % molybdenum, greater than or equal to about 50 atomic % molybdenum, greater than or equal to about 60 atomic % molybdenum, greater than or equal to about 70 atomic % molybdenum, greater than or equal to about 80 atomic % molybdenum, greater than or equal to about 90 atomic % molybdenum, or greater than or equal to about 95 atomic % molybdenum. In some embodiments, the molybdenum-containing film comprises one or more of molybdenum metal (elemental molybdenum), molybdenum oxide ($MoO_x$), molybdenum carbide ($MoC_x$), molybdenum silicide ($MoSi_x$), molybdenum sulfide ($MoS_x$), or molybdenum nitride ($MoN_x$).

The skilled artisan will recognize that the use of molecular formula like $MoSi_x$ does not imply a specific stoichiometric relationship between the elements but merely the identity of the major components of the film. For example, $MoSi_x$ refers to a film whose major composition comprises molybdenum and silicon atoms. In some embodiments, the major composition of the specified film (i.e., the sum of the atomic percent of the specified atoms) is greater than or equal to about 95%, 98%, 99% or 99.5% of the film, on an atomic basis.

With reference to FIG. 1, one or more embodiments of the disclosure are directed to method 100 of depositing a film. The method illustrated in FIG. 1 is representative of an atomic layer deposition (ALD) process in which the substrate or substrate surface is exposed sequentially to the reactive gases in a manner that prevents or minimizes gas phase reactions of the reactive gases. In some embodiments, the method comprises a chemical vapor deposition (CVD) process in which the reactive gases are mixed in the processing chamber to allow gas phase reactions of the reactive gases and deposition of the thin film.

In some embodiments, the method 100 optionally includes a pre-treatment operation 105. The pre-treatment can be any suitable pre-treatment known to the skilled artisan. Suitable pre-treatments include, but are not limited to, pre-heating, cleaning, soaking, native oxide removal, or deposition of an adhesion layer (e.g., titanium nitride (TiN)). In one or more embodiments, an adhesion layer, such as titanium nitride, is deposited at operation 105. In other embodiments, an adhesion layer is not deposited.

At deposition 110, a process is performed to deposit a molybdenum-containing film on the substrate (or substrate surface). The deposition process can include one or more operations to form a film on the substrate. In operation 112, the substrate (or substrate surface) is exposed to a molybdenum precursor to deposit a film on the substrate (or substrate surface). The molybdenum precursor can be any suitable molybdenum-containing compound that can react with (i.e., adsorb or chemisorb onto) the substrate surface to leave a molybdenum-containing species on the substrate surface.

Current molybdenum precursors for ALD of metallic films use halogen and carbonyl-based substituents, which provide sufficient stability at the expense of reduced reactivity, increasing process temperature. Other molybdenum precursors include anionic nitrogen ligands, which may lead to the formation of nitride impurities. Accordingly, one or more embodiments use 2n-electron donor neutral mono-, bi-, and tri-dentate ligand ligands to form thermally stable complexes. The hydrogen bonding between the ligands provides additional stability. This combination gives provides molybdenum precursors having improved thermal stability, while retaining high volatility.

In one or more embodiments, the molybdenum precursor, specifically molybdenum(0) precursors, has a structure of Formula (I), Formula (II), or Formula (III):

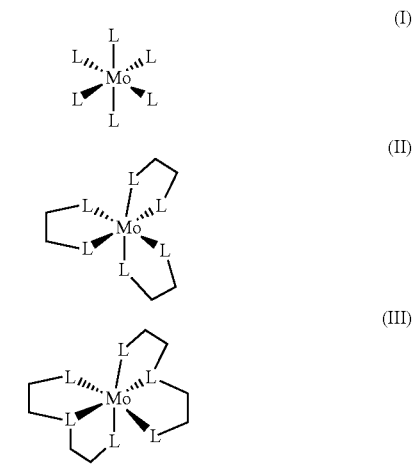

wherein L is one or more of a 2n-electron donor neutral monodentate ligand, 2n-electron donor neutral bidentate ligand, and a 2n-electron donor neutral tridentate ligand. In some embodiments, L is independently selected from the group consisting of alkene, amine, carbonyl, phosphine, and crown sulfur. The metal coordination complex may be substantially free of halogen and substantially free of a Mo—O bond.

Unless otherwise indicated, the term "lower alkyl," "alkyl," or "alk" as used herein alone or as part of another group includes both straight and branched chain hydrocarbons, containing 1 to 20 carbons, or 1 to 10 carbon atoms, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Such groups may optionally include up to 1 to 4 substituents. The alkyl may be substituted or unsubstituted.

In one or more embodiments, the metal coordination complex comprises a structure of Formula (I), Formula (II), or Formula (III). The structure of Formula (I), Formula (II), and Formula (III) may be selected from the group consisting of: $Mo(CO)_n(PMe_3)_{(6-n)}$ wherein n is from 1 to 3, $Mo(CO)_n(CNMe)_{(6-n)}$ wherein n is from 1 to 3, $Mo(CO)_n(Py)_{(6-n)}$ wherein n is from 1 to 3, $Mo(CO)_n(SMe_2)_{(6-n)}$ wherein n is from 1 to 3,

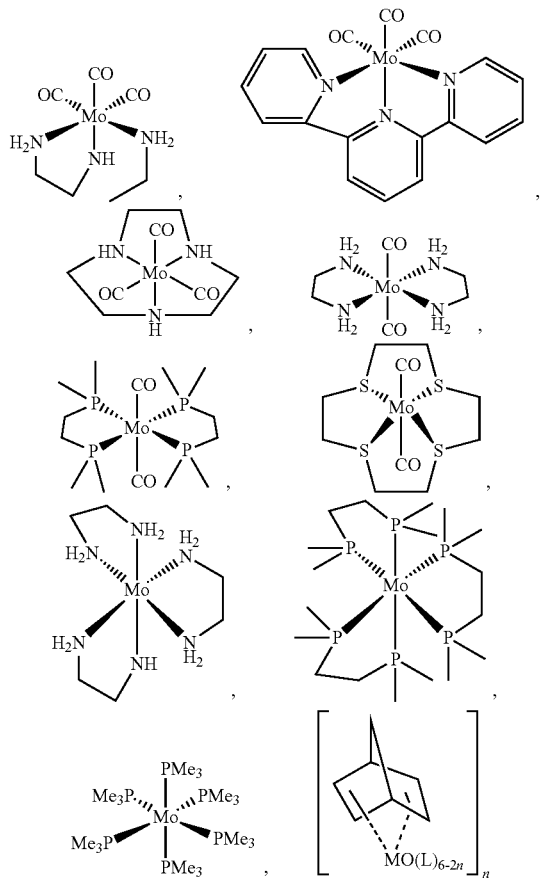

wherein n is from 1 to 3, and

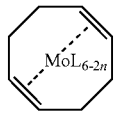

wherein n is from 1 to 3.

As used herein, a "substrate surface" refers to any substrate surface upon which a layer may be formed. The substrate surface may have one or more features formed therein, one or more layers formed thereon, and combinations thereof. The substrate (or substrate surface) may be pretreated prior to the deposition of the molybdenum-containing layer, for example, by polishing, etching, reduction, oxidation, halogenation, hydroxylation, annealing, baking, or the like.

The substrate may be any substrate capable of having material deposited thereon, such as a silicon substrate, a III-V compound substrate, a silicon germanium (SiGe) substrate, an epi-substrate, a silicon-on-insulator (SOI) substrate, a display substrate such as a liquid crystal display (LCD), a plasma display, an electro luminescence (EL) lamp display, a solar array, solar panel, a light emitting diode (LED) substrate, a semiconductor wafer, or the like. In some embodiments, one or more additional layers may be disposed on the substrate such that the molybdenum-containing layer may be at least partially formed thereon. For example, in some embodiments, a layer comprising a metal, a nitride, an oxide, or the like, or combinations thereof may be disposed on the substrate and may have the molybdenum containing layer formed upon such layer or layers.

At operation 114, the processing chamber is optionally purged to remove unreacted molybdenum precursor, reaction products and by-products. As used in this manner, the term "processing chamber" also includes portions of a processing chamber adjacent the substrate surface without encompassing the complete interior volume of the processing chamber. For example, in a sector of a spatially separated processing chamber, the portion of the processing chamber adjacent the substrate surface is purged of the molybdenum precursor by any suitable technique including, but not limited to, moving the substrate through a gas curtain to a portion or sector of the processing chamber that contains none or substantially none of the molybdenum precursor. In one or more embodiments, purging the processing chamber comprises applying a vacuum. In some embodiments, purging the processing chamber comprises flowing a purge gas over the substrate. In some embodiments, the portion of the processing chamber refers to a micro-volume or small volume process station within a processing chamber. The term "adjacent" referring to the substrate surface means the physical space next to the surface of the substrate which can provide sufficient space for a surface reaction (e.g., precursor adsorption) to occur. In one or more embodiments, the purge gas is selected from one or more of nitrogen ($N_2$), helium (He), and argon (Ar).

At operation 116, the substrate (or substrate surface) is exposed to a reactant to form one or more of a molybdenum film on the substrate. The reactant can react with the molybdenum-containing species on the substrate surface to form the molybdenum-containing film. In some embodiments, the reactant comprises a reducing agent. In one or more embodiments, the reducing agent can comprise any reducing agent known to one of skill in the art. In other embodiments, the reactant comprises an oxidizing agent. In one or more embodiments, the oxidizing agent can comprise any oxidizing agent known to one of skill in the art. In further embodiments, the reactant comprises one or more of oxidizing agent and a reducing agent.

In specific embodiments, the reactant is selected from one or more of 1,1-dimethylhydrazine (DMH), alkyl amine, hydrazine, alkyl hydrazine, allyl hydrazine, hydrogen ($H_2$), ammonia ($NH_3$), alcohols, water ($H_2O$), oxygen ($O_2$), ozone ($O_3$), nitrous oxide ($N_2O$), nitrogen dioxide ($NO_2$), peroxides, N-oxides (e.g., $Me_3NO$, TEMPO), P-oxide (e.g., $Et_3PO$), S-oxides, and plasmas thereof. In some embodiments, the alkyl amine is selected from one or more of tert-butyl amine ($tBuNH_2$), isopropyl amine ($iPrNH_2$), ethylamine ($CH_3CH_2NH_2$), diethylamine ($(CH_3CH_2)_2NH$), or butyl amine ($BuNH_2$). In some embodiments, the reactant comprises one or more of compounds with the formula $R'NH_2$, $R'_2NH$, $R'_3N$, $R'_2SiNH_2$, $(R'_3Si)_2NH$, $(R'_3Si)_3N$; where each R' is independently H or an alkyl group having 1-12 carbon atoms. In some embodiments, the alkyl amine consists essentially of one or more of tert-butyl amine ($tBuNH_2$), isopropyl amine ($iPrNH_2$), ethylamine ($CH_3CH_2NH_2$), diethylamine ($(CH_3CH_2)_2NH$), butyl amine ($BuNH_2$).

At operation 118, the processing chamber is optionally purged after exposure to the reactant. Purging the processing chamber in operation 118 can be the same process or different process than the purge in operation 114. Purging the processing chamber, portion of the processing chamber, area adjacent the substrate surface, etc., removes unreacted reactant, reaction products and by-products from the area adjacent the substrate surface.

At decision 120, the thickness of the deposited film, or number of cycles of molybdenum-precursor and reactant is considered. If the deposited film has reached a predetermined thickness or a predetermined number of process cycles have been performed, the method 100 moves to an optional post-processing operation 130. If the thickness of the deposited film or the number of process cycles has not reached the predetermined threshold, the method 100 returns to operation 110 to expose the substrate surface to the molybdenum precursor again in operation 112 and continuing.

The optional post-processing operation 130 can be, for example, a process to modify film properties (e.g., annealing) or a further film deposition process (e.g., additional ALD or CVD processes) to grow additional films. In some embodiments, the optional post-processing operation 130 can be a process that modifies a property of the deposited film. In some embodiments, the optional post-processing operation 130 comprises annealing the as-deposited film. In some embodiments, annealing is done at temperatures in the range of about 300° C., 400° C., 500° C., 600° C., 700° C., 800° C., 900° C. or 1000° C. The annealing environment of some embodiments comprises one or more of an inert gas (e.g., molecular nitrogen ($N_2$), argon (Ar)) or a reducing gas (e.g., molecular hydrogen ($H_2$) or ammonia ($NH_3$)) or an oxidant, such as, but not limited to, oxygen ($O_2$), ozone ($O_3$), or peroxides. Annealing can be performed for any suitable length of time. In some embodiments, the film is annealed for a predetermined time in the range of about 15 seconds to about 90 minutes, or in the range of about 1 minute to about 60 minutes. In some embodiments, annealing the as-deposited film increases the density, decreases the resistivity and/or increases the purity of the film.

The method 100 can be performed at any suitable temperature depending on, for example, the molybdenum precursor, reactant, or thermal budget of the device. In one or more embodiments, the use of high temperature processing may be undesirable for temperature-sensitive substrates, such as logic devices. In some embodiments, exposure to the molybdenum precursor (operation 112) and the reactant (operation 116) occur at the same temperature. In some embodiments, the substrate is maintained at a temperature in a range of about 20° C. to about 400° C., or about 50° C. to about 650° C.

In some embodiments, exposure to the molybdenum precursor (operation 112) occurs at a different temperature than the exposure to the reactant (operation 116). In some embodiments, the substrate is maintained at a first temperature in a range of about 20° C. to about 400° C., or about 50° C. to about 650° C., for the exposure to the molybdenum precursor, and at a second temperature in the range of about 20° C. to about 400° C., or about 50° C. to about 650° C., for exposure the reactant.

In the embodiment illustrated in FIG. 1, at deposition operation 110 the substrate (or substrate surface) is exposed to the molybdenum precursor and the reactant sequentially. In another, un-illustrated, embodiment, the substrate (or substrate surface) is exposed to the molybdenum precursor and the reactant simultaneously in a CVD reaction. In a CVD reaction, the substrate (or substrate surface) can be exposed to a gaseous mixture of the molybdenum precursor and reactant to deposit a molybdenum-containing film having a predetermined thickness. In the CVD reaction, the molybdenum-containing film can be deposited in one exposure to the mixed reactive gas or can be multiple exposures to the mixed reactive gas with purges between.

In some embodiments, the molybdenum-containing film formed comprises elemental molybdenum. Stated differently, in some embodiments, the molybdenum-containing film comprises a metal film comprising molybdenum. In some embodiments, the metal film consists essentially of molybdenum. As used in this manner, the term "consists essentially of molybdenum" means that the molybdenum-containing film is greater than or equal to about 80%, 85%, 90%, 95%, 98%, 99% or 99.5% A molybdenum, on an atomic basis. Measurements of the composition of the molybdenum-containing film refer to the bulk portion of the film, excluding interface regions where diffusion of elements from adjacent films may occur.

In other embodiments, the molybdenum-containing film comprises molybdenum oxide ($MoO_x$) with an oxygen content of greater than or equal to about 5%, 7.5%, 10%, 12.5% or 15%, on an atomic basis. In some embodiments, the molybdenum-containing film comprises an oxygen content in the range of about 2% to about 30%, or in the range of about 3% to about 25%, or in the range of about 4% to about 20%, on an atomic basis.

In other embodiments, the molybdenum-containing film comprises molybdenum carbide ($MoC_x$) with a carbon content of greater than or equal to about 5%, 7.5%, 10%, 12.5 or 15%, on an atomic basis. In some embodiments, the molybdenum-containing film comprises a carbon content in the range of about 2% to about 30%, or in the range of about 3% to about 25%, or in the range of about 4% to about 20%, on an atomic basis.

The deposition operation 110 can be repeated to form one or more of a molybdenum oxide film, a molybdenum carbide film, a molybdenum silicide film, a molybdenum disulfide film, and a molybdenum nitride film, having a predetermined thickness. In some embodiments, the deposition operation 110 is repeated to provide one or more of a molybdenum oxide film, a molybdenum carbide film, a molybdenum silicide film, and a molybdenum nitride film having a thickness in the range of about 0.3 nm to about 100 nm, or in the range of about 30 Å to about 10 µM.

One or more embodiments of the disclosure are directed to methods of depositing molybdenum-containing films in high aspect ratio features. A high aspect ratio feature is a trench, via or pillar having a height:width ratio greater than or equal to about 10, 20, or 50, or more. In some embodiments, the molybdenum-containing film is deposited conformally on the high aspect ratio feature. As used in this manner, a conformal film has a thickness near the top of the feature that is in the range of about 80-120% of the thickness at the bottom of the feature.

Some embodiments of the disclosure are directed to methods for bottom-up gapfill of a feature. A bottom-up gapfill process fills the feature from the bottom versus a conformal process which fills the feature from the bottom and sides. In some embodiments, the feature has a first material at the bottom (e.g., a nitride) and a second material (e.g., an oxide) at the sidewalls. The molybdenum-containing film deposits selectively on the first material relative to the second material so that the molybdenum film fills the feature in a bottom-up manner.

According to one or more embodiments, the substrate is subjected to processing prior to and/or after forming the layer. This processing can be performed in the same chamber or in one or more separate processing chambers. In some embodiments, the substrate is moved from the first chamber to a separate, second chamber for further processing. The substrate can be moved directly from the first chamber to the separate processing chamber, or it can be moved from the first chamber to one or more transfer chambers, and then moved to the separate processing chamber. Accordingly, the processing apparatus may comprise multiple chambers in communication with a transfer station. An apparatus of this sort may be referred to as a "cluster tool" or "clustered system," and the like.

Generally, a cluster tool is a modular system comprising multiple chambers which perform various functions including substrate center-finding and orientation, degassing, annealing, deposition and/or etching. According to one or more embodiments, a cluster tool includes at least a first chamber and a central transfer chamber. The central transfer chamber may house a robot that can shuttle substrates between and among processing chambers and load lock chambers. The transfer chamber is typically maintained at a vacuum condition and provides an intermediate stage for shuttling substrates from one chamber to another and/or to a load lock chamber positioned at a front end of the cluster tool. Two well-known cluster tools which may be adapted for the present disclosure are the Centura® and the Endura®, both available from Applied Materials, Inc., of Santa Clara, Calif. However, the exact arrangement and combination of chambers may be altered for purposes of performing specific steps of a process as described herein. Other processing chambers which may be used include, but are not limited to, cyclical layer deposition (CLD), atomic layer deposition (ALD), chemical vapor deposition (CVD), physical vapor deposition (PVD), etch, pre-clean, chemical clean, thermal treatment such as RTP, plasma nitridation, degas, orientation, hydroxylation, and other substrate processes. By carrying out processes in a chamber on a cluster tool, surface contamination of the substrate with atmospheric impurities can be avoided without oxidation prior to depositing a subsequent film.

According to one or more embodiments, the substrate is continuously under vacuum or "load lock" conditions and is not exposed to ambient air when being moved from one chamber to the next. The transfer chambers are thus under vacuum and are "pumped down" under vacuum pressure. Inert gases may be present in the processing chambers or the transfer chambers. In some embodiments, an inert gas is used as a purge gas to remove some or all of the reactants (e.g., reactant). According to one or more embodiments, a purge gas is injected at the exit of the deposition chamber to prevent reactants (e.g., reactant) from moving from the deposition chamber to the transfer chamber and/or additional processing chamber. Thus, the flow of inert gas forms a curtain at the exit of the chamber.

The substrate can be processed in single substrate deposition chambers, where a single substrate is loaded, processed, and unloaded before another substrate is processed. The substrate can also be processed in a continuous manner, similar to a conveyer system, in which multiple substrates are individually loaded into a first part of the chamber, move through the chamber, and are unloaded from a second part of the chamber. The shape of the chamber and associated conveyer system can form a straight path or curved path. Additionally, the processing chamber may be a carousel in which multiple substrates are moved about a central axis and are exposed to deposition, etch, annealing, cleaning, etc. processes throughout the carousel path.

During processing, the substrate can be heated or cooled. Such heating or cooling can be accomplished by any suitable means including, but not limited to, changing the temperature of the substrate support, and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated (about the substrate axis) continuously or in discrete steps. For example, a substrate may be rotated throughout the entire process, or the substrate can be rotated by a small amount between exposures to different reactive or purge gases. Rotating the substrate during processing (either continuously or in steps) may help produce a more uniform deposition or etch by minimizing the effect of, for example, local variability in gas flow geometries.

The disclosure is now described with reference to the following examples. Before describing several exemplary embodiments of the disclosure, it is to be understood that the disclosure is not limited to the details of construction or process steps set forth in the following description. The disclosure is capable of other embodiments and of being practiced or being carried out in various ways.

EXAMPLES

Example 1: Preparation of $Mo(CO)_3(PMe_3)_3$ $Mo(CO)_3(PMe_3)_3$ was prepared by reacting $Mo(CO)_6$ with 3 equivalents of trimethylphosphine in acetonitrile at 90° C. for 3 hours. The removal of acetonitrile under vacuum provided the target precursor $Mo(CO)_3(PMe_3)_3$ as a solid in 88% yield with a purity of 98%. Melting point 35° C.

$^1$H NMR ($C_6D_6$, 500 MHz, ppm): δ 0.76-0.74 (d, $CH_3$, $J_{P-H}$=10 Hz)

$^{13}$C NMR ($C_6D_6$, 500 MHz, ppm): δ 206.0 (s, CO), 19.3 (s, CH3)

$^{31}$P NMR ($C_6D_6$, 500 MHz, ppm): δ −16.9

Example 2: Preparation of Additional Molybdenum Precursors

Similar to $Mo(CO)_3(PMe_3)_3$, other precursors would be prepared by reacting $Mo(CO)_6$ with the corresponding ligands.

Example 3: Atomic Layer Deposition of Molybdenum Containing Films

General procedure: A silicon substrate was placed in a processing chamber. A molybdenum precursor was flowed into the processing chamber in an atmosphere of nitrogen ($N_2$) gas over the silicon substrate leaving a molybdenum-precursor terminated surface. Unreacted precursor and byproducts were then purged out of the chamber. Next, a co-reactant was then introduced into the chamber that reacted with the surface-bound molybdenum species. Again, excess coreactant and byproducts were removed from the chamber. The resultant material on the substrate was a molybdenum-containing film.

Spatially relative terms, such as "beneath," "below," "lower," "above," "upper" and the like, may be used herein for ease of description to describe one element or feature's

What is claimed is:

1. A metal coordination complex comprising molybdenum(0) and having a structure selected from the group consisting of: $Mo(CO)_n(CNMe)_{(6-n)}$ wherein n is from 1 to 3, $Mo(CO)_n(Py)_{(6-n)}$ wherein n is from 1 to 3, $Mo(CO)n(SMe_2)_{(6-n)}$ wherein n is from 1 to 3,

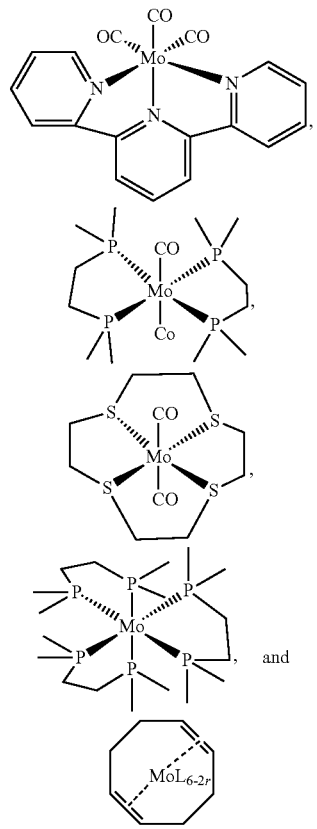

wherein n is from 1 to 3, wherein the metal coordination complex is substantially free of halogen and substantially free of a Mo-O bond, and wherein L is selected from the group consisting of a 2n-electron donor neutral monodentate ligand, a 2n-electron donor neutral bidentate ligand, a 2n-electron donor neutral tridentate ligand, and combinations thereof.

* * * * *